(12) United States Patent
van't Hooft et al.

(10) Patent No.: US 7,645,224 B2
(45) Date of Patent: Jan. 12, 2010

(54) APPARATUS FOR TRANSPORTING AND POSITIONING A CAPSULE IN WHICH A RADIOACTIVE SOURCE IS PRESENT

(75) Inventors: Eric van't Hooft, Brasschaat (BE); Libbe van Zwol, Veenendall (NL); Joeri Tuijn, Utrecht (NL)

(73) Assignee: Isodose Control Intellectual Property B.V., Veenendaal (NL)

(*) Notice: Subject to any disclaimer, the term of this patent is extended or adjusted under 35 U.S.C. 154(b) by 897 days.

(21) Appl. No.: 11/123,261

(22) Filed: May 6, 2005

(65) Prior Publication Data
US 2005/0261539 A1 Nov. 24, 2005

(30) Foreign Application Priority Data
May 6, 2004 (NL) .................................. 1026130

(51) Int. Cl.
*A61N 5/00* (2006.01)
(52) U.S. Cl. .............................................. 600/3; 600/7
(58) Field of Classification Search .................. 600/1–8
See application file for complete search history.

(56) References Cited
U.S. PATENT DOCUMENTS
4,897,076 A * 1/1990 Puthawala et al. ............. 600/7
5,030,194 A * 7/1991 Van't Hooft et al. .......... 600/3
6,440,058 B1 * 8/2002 Cutrer ............................ 600/8
6,497,645 B1 * 12/2002 Halpern ........................ 600/3

FOREIGN PATENT DOCUMENTS
DE 0523417 * 1/1993

* cited by examiner

*Primary Examiner*—Charles A Marmor, II
*Assistant Examiner*—Carrie Harris
(74) *Attorney, Agent, or Firm*—Leydig, Voit & Mayer Ltd

(57) ABSTRACT

An apparatus is described for transporting and positioning a capsule, in which a radioactive source is present, from a screened safe into an applicator to be temporarily placed in the body of the patient. The apparatus is provided with a safe for storing at least one capsule and with a larger number of applicators, which can be connected, via transport tubes, to passages in a switch-connecting plate, wherein the capsules, or a dummy instead of one of the capsules, can each, via their own tube and switch, independently of one another, be introduced into a transport tube selected by the respective switch and can be displaced therein independently of one another in a manner programmable with regard to location and residence time, by a transport wire slidable via a drive motor.

10 Claims, 2 Drawing Sheets

Fig. 3

|     | 1  | 2  | 3  | 4  | 5  | 6  |
|-----|----|----|----|----|----|----|
|     |    | 5  | 5  |    |    |    |
| 10  |    |    |    |    |    |    |
|     |    | 5  | 5  | 5  | 5  | 5  |
|     | 10 | 10 | 10 | 10 | 10 | 10 |

Location

Table 1 illustrating the treatment schedule of sources 10 and 5.

| Source \ Treatment Time | 1 | 2 | 3 | 4 | 5 | 6 | 7 |
|---|---|---|---|---|---|---|---|
| 10 | 1 | 1 | 2 | 3 | 4 | 5 | 6 |
| 5  | 6 | 5 | 4 | 2 | 2 | 3 | 3 |

Table 2 illustrating the schedule of locations for the treatment schedule in Table 1.

US 7,645,224 B2

APPARATUS FOR TRANSPORTING AND POSITIONING A CAPSULE IN WHICH A RADIOACTIVE SOURCE IS PRESENT

CROSS-REFERENCE TO RELATED APPLICATION

This application claims priority of Netherlands Application NL 1026130, filed on May 6, 2004, the contents of which are expressly incorporated herein by reference in their entirety including the contents and teachings of any references contained therein.

FIELD OF THE INVENTION

The invention generally relates to apparatuses for transporting and positioning a capsule, in which a radioactive source is present, from a screened safe into an applicator to be temporarily placed in the body of the patient.

BACKGROUND OF THE INVENTION

One such apparatus of the type generally referred to above is described within DE 41.23.501 describing an apparatus including: a capsule connected with one end of a transport wire, which is slidable by a drive motor; a safe for storage of the capsule and provided with a channel from taking the capsule into and out of the safe via the transport wire; at least one applicator; a number of transport wires corresponding with the number of applicators, which each have a first end connected to an applicator; a switch-connecting plate with multiple passages, wherein each second end of each transport tube is connected to a passage; a switch with a passageway which, on the one hand, can successively be brought into a position in line with one of the passages in the switch-connecting plate and, on the other hand, connects to a first end of a tube whose other end connects to the channel through the safe; and at least one farther switch with a passageway, which can be brought in line with one of the passages in the switch-connecting plate, just like the passageway of the first switch, so that a further capsule on a further transport wire can be displaced by a further drive motor through the transport tube connecting to the passage selected by the position of the further switch.

With such an apparatus, a capsule can be introduced into an applicator to be selected by setting of the switch and can be stopped at different locations to locally effect a concentrated radiation in the body of a patient. Said publication discloses an independently controlled switch to guide a dummy capsule into the applicator for testing purposes. With increasing age of the radioactive source, the dose rate released by the capsule decreases, as a result of which the radiation time needs to be prolonged. If this dose rate is too low, the capsule with the radioactive source present therein needs to be replaced.

SUMMARY OF THE INVENTION

The invention contemplates improving upon an apparatus of the type described in the opening paragraph such that the radiation time can always remain as short as possible in the course of time and, at the same time, the capsule can be utilized as optimally as possible.

This is achieved according to the invention by providing the apparatus with actuators for actuating said switches and said transport wires, said actuators being programmable so that, from the safe, via the tube, the passageway, a passage determined by the position of the switch and a transport tube connected thereto, said capsules can be introduced into an applicator and can be withdrawn into the safe again, in a manner independent of other capsules with regard to location and residence time. These measures, which can be realized with relatively small extra purchasing costs, make it possible to select a specific radiation to be carried out for a combined radiation via multiple older and/or younger capsules, so that, on the one hand, the radiation time can be minimized and, on the other hand, also, effective use can still be made of older capsules, which is advantageous both with a view to costs and to the environment.

The apparatus embodying the present invention has additional advantages. By using a further drive motor, the possibility of further variation of the radiation pattern is obtained, in that, for instance, isotopes can be combined, the energy per isotope being different. It is thus possible to radiate locally with a lower depth dose, so that organs in the human body can be spared.

By using the capsules for a longer time giving a higher dose or in larger volume implants, further, the advantage of a greater versatility of the apparatus is obtained. Because capsules with relatively low energy are available as well, it is further possible to use the apparatus in a slightly screened operating room.

A further advantage of using a further drive motor is that it can substantially reduce waiting time for hospital staff. For most treatments, use can be made of multiple applicator tubes, for instance to irradiate a larger volume tumor. Prior to directing a capsule through a transport tube, it can be checked using a dummy whether the path through the transport tube and the applicator is clear of obstacles, as caused by a kinked or bent transport tubes and applicators. If a treatment needs to take place with a multiple number of applicator tubes, then, during the carrying out of a treatment, it can be checked using a dummy whether the path through a further transport tube and the applicator is clear for the next treatment. Thus, the total time of a treatment session can be reduced, so that more treatments can be carried out per time unit, which improves both productivity and efficiency.

As an applicator, a hollow needle can be used, which is couplable with a transport tube. In order to be able to carry out a treatment as optimally as possible with as few harmful side effects as possible, multiple needles can be provided around a tumor, such as for instance up to 40 needles. In order to be able to further optimize the radiation pattern in the presence of at least one further drive motor, so that different applicators can simultaneously be placed in mutually different capsules, it is preferred according to a further embodiment of the invention that the drive motors are servomotors or stepping motors, which are able to place the capsules in, for instance, 1 to 400 different positions, so that, particularly with combined radiation, a large variety of radiation patterns are possible in that location, residence time and displacement of the capsules relative to one another are changeable. When the apparatus is not in use or when an applicator is placed, the radioactive source capsules are stored in a screened safe. For placing an applicator and determining a radiation schedule, use can be made of the dummy, which is also used for testing whether the path for a capsule is clear. As is well-known, such a dummy can be kept outside the storage holder if desired. By displacing the dummy in addition to two or more capsules with their own drive motors, a further optimization with regard to combined radiation and reducing the total treatment time can be obtained.

Taking, as desired, two or more capsules and optionally also a dummy to different transport tubes to be selected from a series of transport tubes is made possible by using a number of switches. In order to be able to operate in an optimal manner, it is preferred according to a further embodiment of the invention that each switch is provided with a connecting element, the connecting elements of the respective switches being displaceable independently of one another. Thus, a maximum freedom is obtained with regard to radiation, positioning and testing operations. An option to be considered here are connecting elements whose passageways are sendingly displaceable on, for instance, multiple levels on the switch-connecting plate. According to a further embodiment of the invention, however, it is preferred that the connecting elements are mutually independent pivoting arms, which are provided with a passageway and are pivotable about a common centerline, around which common centerline the passages are arranged so as to be radially symmetrical with their centerlines and parallel to that common centerline. By a simple pivotal movement, the desired transport tube can then be approached. In order to save costs, it is preferred that the individually drivable pivoting arms are alternately drivable by the same motor, which can be realized by means of a simple sliding coupling and is partly made possible by the fact that simultaneously approaching two transport tubes is no requirement.

In order to guarantee an exact connection between a passageway and a tube, according to a further embodiment of the invention, it can be provided that the pivoting arms are controlledly displaceable in the direction of the common centerline, which can be carried out quickly and controlledly in an effective manner if a pulling magnet is present for being able to displace them in a controlled manner, which magnet can displace each of the pivoting arms, which are forced in the direction of the common centerline towards the switch-connecting plate, individually in opposite direction.

In view of the nature of the objects to be transported, capsules in which a radioactive source is present, it is important to know when a capsule has left the safe and when it has returned therein again. For this purpose, it is further proposed according to the invention that, in or near a passageway or passage, a detector, preferably mounted on a connecting element, is provided for recording whether or not a capsule, a dummy or a radioactive source passes. Further, this detector can be deployed for checking whether the capsule sees the source pass at the right moment on its way to the applicator. Further, the detector serves to check whether the transport tube has been connected correctly and whether the right channel has been connected through.

In another aspect, the invention relates to a method of operating an apparatus according to any one of the preceding claims, wherein said method comprises: determining for each location a desired radiation dose to be received; selecting for each of said locations a number of capsules each having a predetermined dose rate; determining a radiation schedule for each of said number of capsules; and calculating for each of said number of capsules a corresponding residence time in each of said locations.

BRIEF DESCRIPTION OF THE DRAWINGS

The appended claims set forth the features of the present invention with particularity. The invention, together with its objects and advantages, may be best understood from the following detailed description taken in conjunction with the accompanying drawings of which:

FIG. 3 shows a first and second table example comprising a schematic numerical example of combining multiple capsules in order to reduce treatment time.

DETAILED DESCRIPTION OF THE DRAWINGS

Figure 1:
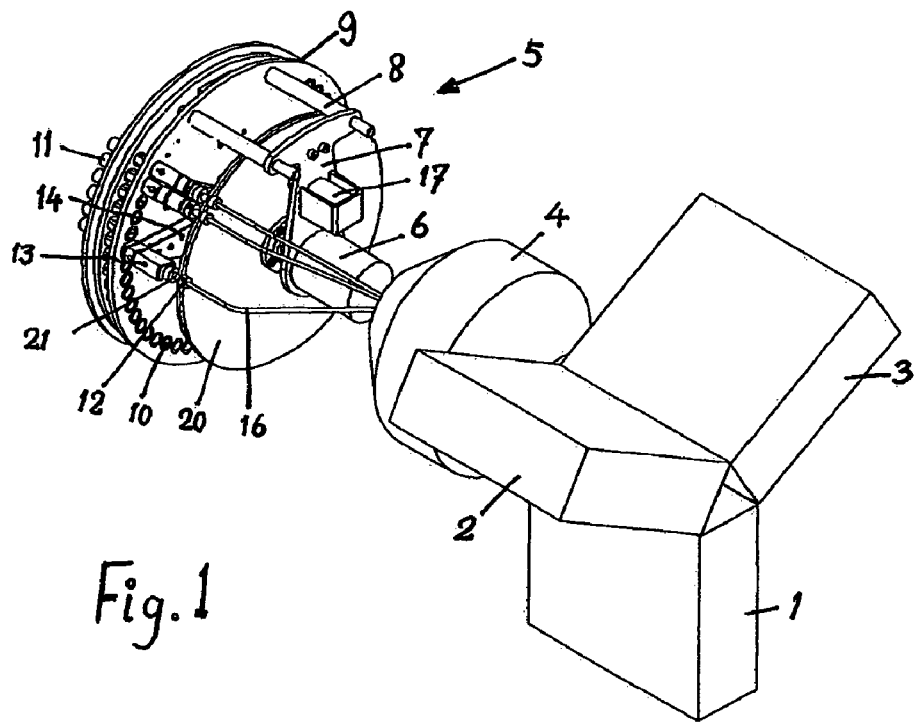
FIG. 1 shows, in perspective, an apparatus according to the invention.

The Figures diagrammatically show three drive units 1, 2 and 3, which are each, in the conventional known manner, provided with inter alia, a drive motor, which is preferably designed as stepping motor and can operate a storage for a transport wire, and a safe 4 for the storage of capsules, in which a radioactive source can be present, and a switch shown in more detail and generally designated by reference numeral 5.

The switch 5 is provided with a motor 6, which is fixedly arranged in a frame of the apparatus not shown in more detail, just like a supporting arm 7, which bears, via two pins 8, a switch-connecting plate 9 formed by a plate assembly, in which a large number of passageways 10 have been provided in a radially symmetrical manner. On a side facing away from the motor 6, a passageway of the passageways 10 terminates in a connecting piece 11 to which, as known per se, a transport tube (not shown) can be connected, which leads to an applicator (not shown either) to be temporarily placed in the body of a patient. Such an applicator may be a hollow needle, which is positioned with respect to a tumor to be radiated. From the side facing away from the connecting piece 11, each passageway 10 is accessible to a coupling element 12, which is slidably received in a guide part 13, each coupling element 12 being spring-loaded with respect to the guide part 13 in such a manner that one end of the coupling element 12 is forced in the direction of the passageways 10. The other end of the coupling element 12 is connected to a tube 16, which is, in turn, connected to an outlet of the safe 4. Each guide part 13 is attached to a pivoting arm 14, which is freely rotatably mounted on shaft 15 of the motor 6.

Normally, a coupling element 12 projects into one of the passageways 10 and thereby connects an outlet of the safe 4 with an applicator via the tube 16, a passageway 10 and a transport tube connecting thereto. A capsule with radioactive source which is present in the safe 4 is connected with the end of a transport wire of one of the drive units 1-3. Using the drive motor of the respective drive unit, the transport wire can be slid such that the capsule is forced out of the safe 4 and is then, via the tube 16, the coupling element 12, the passageway 10 and the transport tube, introduced into the applicator, where the radiation can be carried out in a desired manner for predetermined residence times and from predetermined positions.

It is often preferred to radiate a tumor from different sides and with different intensities. This is possible with the present apparatus in that multiple coupling elements 12 are provided, which can each, with their own pivoting arm 14, be brought in line with a particular passageway 10 leading to a specific applicator. Testing whether the path through a transport tube to an applicator is clear of obstructions, such as bends in the tube, can be carried out using a dummy, which can be directed to the applicator via a transport wire by means of a drive unit 1-3 in the same manner as a capsule. Both carrying out multiple radiations and checking whether the path to the applicator is clear are simultaneously possible in the present apparatus by designing the switch such that, independently of one another, the various coupling elements 12 can be pulled out of a passageway 10 and be brought in line with a different passageway 10.

This mutually independent operation is provided by a pulling magnet 17, which can make a rod 18 pivot about its upper hinge point. The rod 18 is further provided with a lower free end, which engages in a circumferential groove provided in a wheel 19 fixedly attached to the shaft 15 of the motor 6, which wheel is in turn connected with a control plate 20 in the form of a round disc with a radius slightly smaller than the distance to the coupling elements 12 arranged in a radially symmetrical manner. Further, at one location along its circumference, the control plate 20 is provided with a radially projecting cam not shown in the Figures, while each coupling element 12 is provided with a circumferential groove 21, such that the cam can be situated in the circumferential groove 21 by rotation of the control plate 20 with the aid of the motor 6. By energizing the pulling magnet 17 in this situation, the control plate 20 is pulled in the direction of the motor 6 and thereby takes the respective coupling element 12 along through cooperation of the cam and the circumferential groove, so that this element is pulled out of the passageway 10. By then rotating the control plate 20 via the motor 6, the withdrawn coupling element 12 can be brought in line with a different passageway 10, while taking along the freely rotatable pivoting arm 14. Upon withdrawing the control plate 10, the other coupling elements 12 are not affected and the connections with the respective applicators realized thereby are maintained.

Thus, with a minimal loss of time, a number of radiations can be carried out, for instance in that the path to a next location of radiation can already be checked using a dummy while radiation still takes place at a previous location. In this manner, the treatment time can be reduced, which is not only more agreeable to the patient, but also increases the effective operating time of the apparatus and thus reduces the costs.

A very important advantage of the invention is that, by being able to use multiple sources simultaneously, the radiation time can be reduced, while, at the same time, radiation sources can also remain in use longer, for instance by combining an older and a younger source, which is advantageous both with a view to the environment and to costs. In addition, this makes it possible to radiate locally with a lower depth dose, so that organs in the human body are spared and, when using capsules with relatively low energy, the apparatus can also be deployed in a slightly screened operating room.

In the exemplary embodiment shown and discussed, use is made of a switch with a round, rotatable switch-connecting plate. Of course, different embodiments are possible as well. An option to be considered are passageways arranged next to one another in a linear manner, where the coupling elements are taken upwards or downwards for displacing them and are then slid up to the next passage to be used and are there taken upwards or downwards again.

Because the apparatus uses capsules in which a radioactive source is present, it is important to know when a capsule has left the safe 4 and when it has returned therein again. This can be realized by providing a detector, preferably mounted at the location of the guide part 13, which detector can record whether or not a capsule, a dummy or a radioactive source passes. Further, this detector can be deployed for partly determining the location where the capsule is present in the applicator, and whether the right channel is used and is connected in the right manner.

Figure 2:
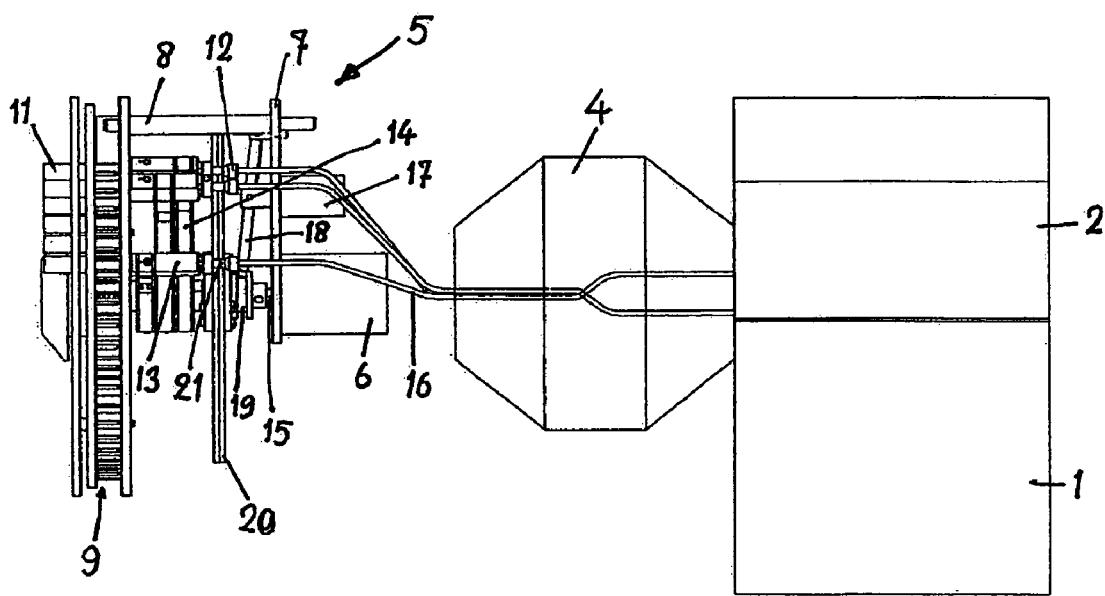
FIG. 2 shows a side elevational view of the apparatus according to FIG. 1.

In an exemplary number embodiment, it is assumed that six locations each need a radiation treatment of 60 (a.u.). A new source is available of 10, an older of 5. In one embodiment, the older source is operated parallel at the same time the new source is active. Hence, a reduction of radiation time can be realized by 33%. In another embodiment, six different locations each need different treatment times, and having three locations of 20 and three locations of 15. According to the invention the embodiments of FIGS. 1 and 2 are equipped with a processor that optimizes a schedule according to a minimal treatment time, treating the locations of 15 in subsequent treatments by sources 10 and 5, and treating the locations of 20 by a combination of sources 10 and 5 in order to keep the treatment time minimal. Again, a reduction of 33% in treatment time is possible. This example is graphically illustrated in FIG. 3.

It goes without saying that, within the framework of the invention, many further modifications and variants are possible in addition to the ones already mentioned hereinabove. Options to be considered are two, four or more coupling elements with associated means. Also, the mechanism for decoupling, and displacing the coupling elements can be realized in many different manners, where an option to be considered is, for instance, being able to withdraw and pivot the pivoting arms individually. Further, in the exemplary embodiment, the three tubes all connect to the outlet of the safe. If one of the tubes is used for directing a dummy, this can also be laid around the safe,

What is claimed is:

1. An apparatus for transporting and positioning a capsule, in which a radioactive source is present, from a screened safe into an applicator to be temporarily placed in the body of the patient, which apparatus is provided with: a capsule connected with one end of a transport wire, which is slidable by a drive motor; a safe for storage of the capsule and provided with a channel for taking the capsule into and out of the safe via the transport wire; at least one applicator; a number of transport tubes corresponding with a number of applicators, which each have a first end connected to an applicator; a switch-connecting plate with multiple passages, wherein each second end of each transport tube is connected to a passage; a switch with a passageway which, on the one hand, can successively be brought into a position in line with one of the passages in the switch-connecting plate and, on the other hand, connects to a first end of a tube whose other end connects to the channel through the safe; at least one further switch with a passageway, which can be brought in line with one of the passages in the switch-connecting plate, in the same manner as like the passageway of the first switch, so that a further capsule on a further transport wire can be displaced by a drive motor through the transport tube connecting to the passage selected by the position of the further switch, wherein each switch is provided with a connecting element, wherein the connecting elements of the respective switches are displaceable independently of one another, the connecting elements are mutually independent pivoting arms, which are provided with a passageway and are pivotable about a common centerline, around which common centerline the passages are arranged so as to be radially symmetrical with their centerlines and parallel to that common centerline, wherein the mutually independent pivoting arms are alternately drivable and the pivoting arms are controlledly displaceable in the direction of the common centerline; actuators for actuating said switches and said transport wires, said actuators being programmable so that, from the safe, via the tube, the passageway, a passage determined by the position of the switch and a transport tube connected thereto, said capsules can be introduced into an applicator and can be withdrawn into the safe again, in a manner independent of other capsules with regard to location and residence time; and said apparatus characterized in that, for enabling controlled displacement, a pulling magnet is present, which can displace each of the pivoting arms, which are forced in the direction of the common centerline towards the switch-connecting plate, individually in opposite direction.

2. The apparatus of claim 1, wherein during the displacement of one of the switches, each further switch remains blocked.

3. The apparatus of claim 1 wherein, in or near a passageway or passage, a detector is arranged for recording whether or not a dummy or a radioactive source passes.

4. The apparatus of claim 3 wherein the detector is mounted on a connecting element.

5. The apparatus of claim 1 wherein the drive motors are stepping motors.

6. The apparatus of claim 1 wherein the safe has multiple channels.

7. The apparatus of the type recited in claim 1 further comprising a processor programmed to control said actuators, said processor carrying out the steps of: determining for each location a desired radiation dose to be received; and selecting for each of said locations a number of capsules each having a predetermined dose rate; determining a radiation schedule for each of said number of capsules; and calculating, for each of said number of capsules, a corresponding residence time in each of said locations.

8. A method of operating the apparatus defined in claim 1, wherein said method comprises: determining for each location a desired radiation dose to be received; and selecting for each of said locations a number of capsules each having a predetermined dose rate; determining a radiation schedule for each of said number of capsules; and calculating, for each of said number of capsules, a corresponding residence time in each of said locations.

9. The method of claim 8, wherein said radiation schedule is determined to minimize a treatment time.

10. A method according to claim 8, wherein said radiation dose delivered originates from different pre-selected isotopes.

* * * * *

UNITED STATES PATENT AND TRADEMARK OFFICE
CERTIFICATE OF CORRECTION

PATENT NO. : 7,645,224 B2  Page 1 of 1
APPLICATION NO. : 11/123261
DATED : January 12, 2010
INVENTOR(S) : van't Hooft et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1239 days.

Signed and Sealed this

Twenty-first Day of December, 2010

David J. Kappos
*Director of the United States Patent and Trademark Office*